(12) United States Patent
Lambino et al.

(10) Patent No.: US 6,646,011 B2
(45) Date of Patent: *Nov. 11, 2003

(54) INSECT REPELLANT COMPOSITIONS

(75) Inventors: Danilo L. Lambino, Quezon City (PH); Kennie U. Dee, Quezon City (PH); Susan M. Niemiec, Yardley, PA (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/089,762

(22) Filed: Jun. 3, 1998

(65) Prior Publication Data

US 2001/0009925 A1 Jul. 26, 2001

(51) Int. Cl.$^7$ .................. A01N 37/18; A01N 25/00; A01N 31/00; A01N 33/00; A01N 37/00
(52) U.S. Cl. .................. 514/625; 424/59; 424/401; 424/405; 424/450; 424/DIG. 10; 514/546; 514/551; 514/557; 514/563; 514/613; 514/725; 514/727; 514/772; 514/772.6; 514/783; 514/873; 514/885; 514/886; 514/887; 514/904; 514/918; 514/919; 514/970; 514/975
(58) Field of Search .................. 424/DIG. 10, 405, 424/450, 59, 401; 514/600, 613, 617, 619, 621, 622, 741, 918, 919, 975, 546, 551, 557, 563, 625, 725, 727, 772, 772.6, 783, 873, 885, 886, 887, 904, 970

(56) References Cited

U.S. PATENT DOCUMENTS

| | | | |
|---|---|---|---|
| 3,803,303 A | 4/1974 | McKibben et al. | 424/84 |
| 4,127,672 A | 11/1978 | Klier et al. | 514/546 |
| 4,756,905 A | 7/1988 | Melnik | 424/63 |
| 4,764,529 A * | 8/1988 | Naik et al. | 514/531 |
| 4,816,256 A * | 3/1989 | Randen | 424/405 |
| 5,039,516 A * | 8/1991 | Goodman et al. | 424/59 |
| 5,057,539 A * | 10/1991 | Neukom et al. | 514/531 |
| 5,443,821 A * | 8/1995 | Smith et al. | 424/65 |
| 5,465,685 A | 11/1995 | Dotolo et al. | 119/651 |
| 5,489,433 A | 2/1996 | Aboud | 424/405 |
| 5,565,208 A | 10/1996 | Vlasblom | 424/405 |
| 5,612,047 A * | 3/1997 | Duffy et al. | 424/405 |
| 5,672,337 A | 9/1997 | Ascione et al. | 424/59 |
| 5,716,602 A | 2/1998 | Uick | 424/59 |

FOREIGN PATENT DOCUMENTS

| | | |
|---|---|---|
| DE | 0 097 813 | 1/1984 |
| EP | 97812 | 1/1984 |
| EP | 97813 | 1/1984 |
| EP | 0 243 694 | 3/1987 |
| GB | 2054377 | 2/1981 |
| JP | 52110824 A | 9/1977 |
| JP | 58198403 | 5/1982 |
| JP | 5092905 A | 4/1993 |
| JP | 5092915 A | 4/1993 |
| WO | WO 98/19537 | 5/1998 |
| WO | WO 98/19538 | 5/1998 |

OTHER PUBLICATIONS

STN/CAS online, file BIOSIS, Acc. No. 1991:481783, Doc. No. BA92:115543 (Ogawa et al., J Pestic. Sci. (1991), 16 (3), 457–464), abstract.*
Qiu et al.,"Formulation of topical insect repellent N,N–diethyl–m–toluamide (DEET): vehicle effects on DEET in vitro skin permeation", International Journal of Pharmaceutics, vol. 163, pp. 167–176 (1998).*
Remington's Pharmaceutical Sciences (17th Ed. 1985), pp. 293–298.*
Formulating Pyrethrum, Issued by the Pyrethrum Bureau, Nakuru, Kenya, 1991.
Merck product brochure entitled Rona Color—Care—Protection—Nov. 1996.
Kirk–Othmer Encyclopedia of Chemical Technology, $3^{rd}$ Edition, vol. 13, John Wiley & Sons, New York, 1981, pp 475–478.
Kirk–Othmer Encyclopedia of Chemical Technology, $3^{rd}$ Edition, Supplement Volume, John Wiley & Sons, New York, 1984, pp 786–805.
Abstract XP–002116426.
Abstract XP–002116427.
Abstract XP–002116428.
Abstract XP–002116429.
Abstract XP–002116425.

* cited by examiner

Primary Examiner—John Pak
Assistant Examiner—Frank Choi
(74) Attorney, Agent, or Firm—Erin M. Harriman

(57) ABSTRACT

The present invention relates to insect repellant compositions containing, based upon the total weight of the composition, from about 6 to about 30 percent by weight of insect repellant active material having functionality selected from ester, amide, urethane or combinations thereof; from about 5 to about 30 percent by weight of alcohol, and from about 1 to about 10 percent by weight of nonionic surfactant. The compositions of the invention exhibit reduced rates of degradation of the active material in solution and are less drying and irritating to sensitive skin.

19 Claims, 4 Drawing Sheets

100 nµ

19 nμ
aggregate

INSECT REPELLANT COMPOSITIONS

FIELD OF THE INVENTION

The present invention relates to methods for repelling insects from a host and compositions effective for the same. More specifically, these compositions have superior stability with respect to degradation of the active material and are gentle to the skin.

BACKGROUND OF THE INVENTION

There are many known insect repellant formulations that use a variety of insect repellant active materials. See, e.g., European patent applications 97,812 and 97,813, and U.S. Pat. Nos. 4,127,672, 4,756,905, 5,465,685, 5,489,433, 5,565,208, 5,672,337 and 5,716,602.

Many of the commercially available insect repellant formulations include insect repellant active materials which contain one or more ester, amide or urethane functionalities. Disadvantageously, these materials are hydrolytically sensitive and often degrade upon long term storage in contact with aqueous media.

Other commercially available insect repellant formulations that contain water insoluble active materials frequently contain a significant amount of solubilizers such as lower monohydric alcohols, i.e., ethanol and isopropanol. However, the amount of such lower alcohols present in these formulations often contributes to drying and irritation of the skin.

It would be desirable to provide a composition that exhibited a reduced rate of decomposition of the insect repellant active material without causing significant drying and irritation to the skin.

SUMMARY OF THE INVENTION

In accordance with the present invention, we have found an insect repellant composition comprising, consisting essentially of, or consisting of, based upon the total weight of the composition:
  a. from about 6 to about 30 percent of insect repellant active material, said active material containing a functionality selected from ester, amide, urethane or combinations thereof;
  b. from about 5 to about 30 percent of alcohol selected from
    i. ethanol;
    ii. isopropanol;
    iii. a glycol monoalkyl ether, said alkyl having from about 1 carbon atom to about 4 carbon atoms;
    iv. a glycol containing from about 3 carbon atoms to about 6 carbon atoms;
    v. oligomers of ethylene glycol or propylene glycol; or
    vi. mixtures thereof; and
  c. from about 1 to about 10 percent by weight of surfactant.

In another embodiment of the present invention we have found a method of reducing the rate of degradation of an insect repellant active material in an aqueous composition, said active material containing functionality selected from ester, amide, urethane or combinations thereof, comprising, consisting of, or consisting essentially of incorporating into the composition under conditions sufficient a degradation-effective amount of a surfactant.

In yet another embodiment of the present invention we have found a method of repelling insects from a host comprising, consisting essentially of, or consisting of: topically applying to the host an insect repellant composition comprising, consisting essentially of, or consisting of, based upon the total weight of the composition:
  a. from about 6 to about 30 percent of insect repellant active material, said active material containing a functionality selected from ester, amide, urethane or combinations thereof;
  b. from about 5 to about 30 percent of alcohol selected from
    i. ethanol;
    ii. isopropanol;
    iii. a glycol monoalkyl ether, said alkyl having from about 1 carbon atom to about 4 carbon atoms;
    iv. a glycol containing from about 3 carbon atoms to about 6 carbon atoms;
    v. oligomers of ethylene glycol or propylene glycol; or
    vi. mixtures thereof; and
  c. from about 1 to about 10 percent by weight of surfactant.

The compositions and methods of this invention provide a unique means for repelling insects with a reduced rate of degradation of the active material but without disadvantageously over-drying or over-irritating the skin.

BRIEF DESCRIPTION OF THE DRAWINGS

The invention will be more fully understood and further advantages will become apparent which reference is made to the following detailed description of the invention and the accompanying drawings in which.

DETAILED DESCRIPTION OF THE INVENTION

Figure 1:
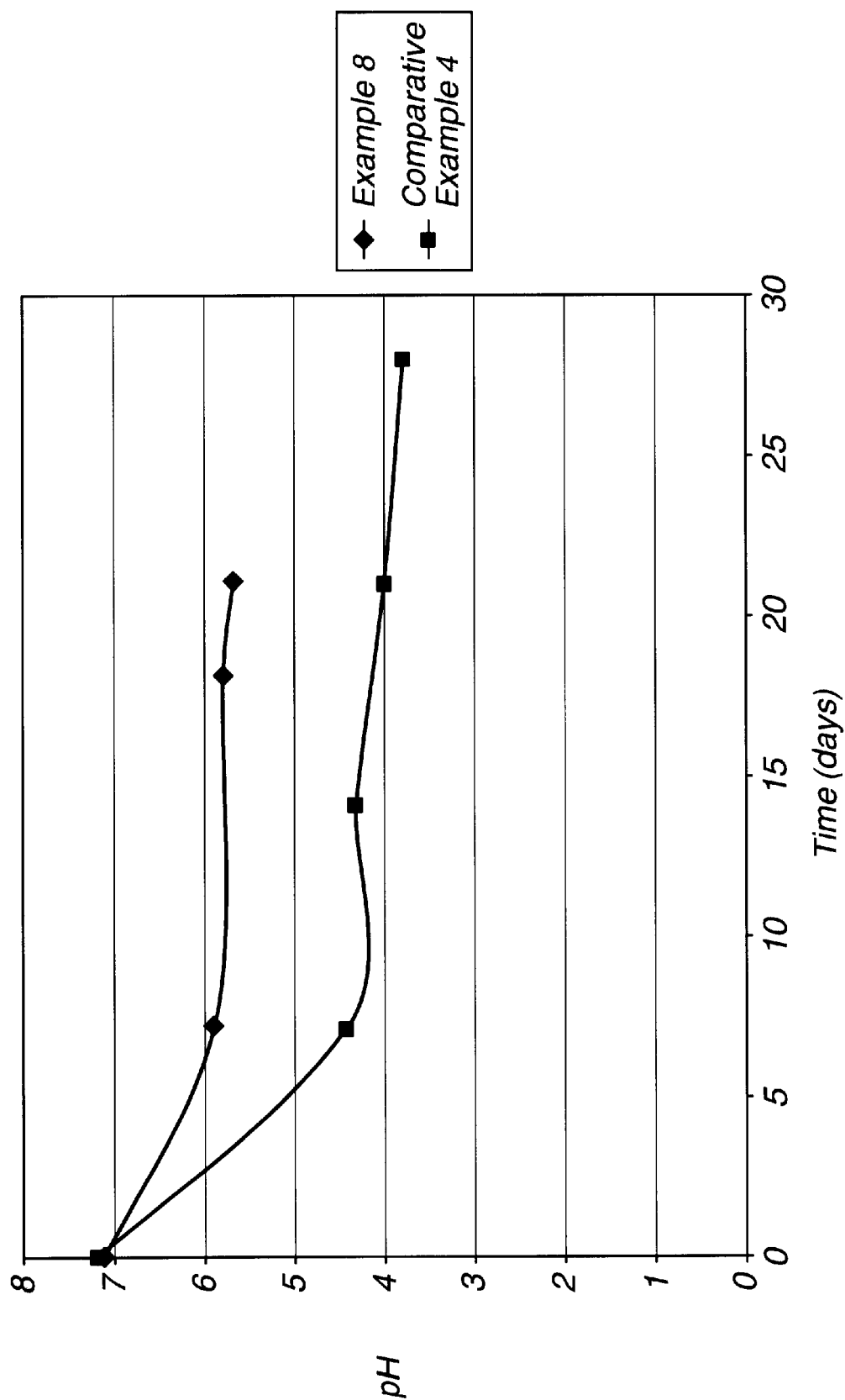
FIG. 1 is a graph depicting the pH stability versus time (days) for a surfactant-free insect repellent composition and for the composition of the present invention.

One aspect of the present invention relates to insect repellant compositions that are useful in repelling insects from a host. By "host," it is meant any plant or being such as humans, mammals, animals, and the like, affected by insects.

The first component of the composition of the present invention is an insect repellant active material containing a functionality selected from ester, amide, urethane or combinations thereof. The insect repellant active material is preferably selected from:

a. N,N-diethyltoluamide,
b. one or more compounds of the formula

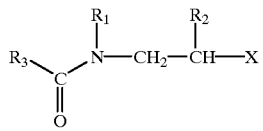

wherein
$R_1$ is a branched or unbranched alkyl group having about 1 to about 6 carbon atoms;
$R_2$ is H, methyl or ethyl;
$R_3$ is a branched or unbranched alkyl or alkoxy group having from about 1 to about 8 carbon atoms; and
X is a —CN or a —COOR$_4$ group, wherein
$R_4$ is a branched or unbranched alkyl group having from about 1 to about 6 carbon atoms;
c. one or more natural or synthetic pyrethroids; or
d. mixtures thereof.

As used herein, N,N-diethyl toluamide refers to the material containing predominantly the meta isomer, i.e., N,N-diethyl-m-toluamide, which is also known as DEET. The natural pyrethroids are contained in pyrethrum, the extract of the ground flowers of *Chrysanthemum cinerariaefolium* or *C coccineum*. Synthetic pyrethroids are synthetically derived, and may be identical structurally or structurally analogous to one or more of the insect repellant active materials found in pyrethrum.

The insect repellent active material is more preferably selected from N,N-diethyltoluamide, ethyl 3-(N-butylacetamido)propionate (formula I above wherein $R_3$ is a $CH_3$ group, $R_1$ is an n-butyl group, $R_2$ is H, X is COOR$_4$ and $R_4$ is ethyl) or mixtures thereof, and most preferably is ethyl 3-(N-butylacetamido)propionate, which is available commercially from Merck KGaA of Darmstadt, Germany under the name, "Insect Repellent 3535."

The particular insects that are repelled by the composition of the present invention will depend upon the insect repellent active material selected. While some insect repellent active materials may be specific to a particular insect species, other active materials may broadly repel a variety of insects. Depending on the active material selected, the compositions has been found to be useful in repelling such insects as ticks, mites, lice, flies, fleas, mosquitoes, and the like.

The compositions of the present invention should contain sufficient amounts of insect repellant active material to be efficacious in repelling the insect over a prolonged period of time following its application to the host. Preferably, the compositions should be efficacious at repelling insects for a period of at least several hours before re-application of the repellant is required. For the active materials disclosed herein, we have found that the insect repellant active material is effective when present in an amount, based upon the total weight of the composition, of from about 6 percent to about 30 percent, preferably from about 10 percent to about 15 percent, and most preferably from about 11 percent to about 14 percent.

The second component of the present invention is at least one alcohol selected from
i. a monohydric alcohol;
ii. a glycol monoalkyl ether having an alkyl group having from about 1 carbon atom to about 4 carbon atoms;
iii. a glycol containing from about 3 to about 6 carbon atoms;
iv. oligomers of ethylene glycol or propylene glycol; or
v. mixtures thereof.

As used herein, the term "monohydric alcohol" refers to a compound containing a single hydroxyl group and the term "glycol" refers to a compound containing two hydroxyl groups. Suitable monohydric alcohols include, but are not limited to, ethanol and isopropanol. Suitable glycol monoalkyl ethers include diethylene glycol monoethyl ether, which has the structure

     IV

This material is known by the Cosmetic, Toiletry, and Fragrance Association (CTFA) name ethoxydiglycol, and is available from the Union Carbide Company of Tarrytown, N.Y. under the tradename, "CARBITOL."

Preferred glycols for use in the compositions of the invention include 1,2-propylene glycol and 1,3-butylene glycol, the latter having the formula:

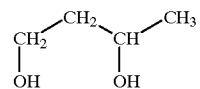     V

Other preferred glycols include 1,2-pentanediol, otherwise known by its CTFA name as pentylene glycol, and 2-methyl-2,4-pentanediol, otherwise known as hexylene glycol, the latter having the formula:

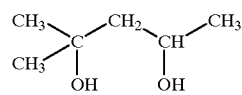     VI

Other alcohols that are useful in the compositions of the present invention include oligomers of ethylene glycol or propylene glycol. Exemplary alcohols that are within this class of materials include diethylene glycol, triethylene glycol, dipropylene glycol, and mixtures thereof.

Preferably the alcohol is a glycol, and more preferably is selected from propylene glycol, butylene glycol, pentylene glycol, hexylene glycol, oligomers of ethylene glycol, oligomers of propylene glycol or mixtures thereof. Of these, butylene glycol is most preferred.

As mentioned above, lower monohydric alcohols have a drying effect when applied to the skin. Accordingly, preferred compositions of the present invention are substantially free of lower monohydric alcohols containing about 2 to about 4 carbon atoms, such as ethanol and isopropanol. By "substantially free" of lower alcohols, it is meant that the compositions should contain, based upon the total weight of the composition, less than about 25 percent, preferably less than about 10 percent, and more preferably less than about 5 percent of such lower alcohols.

The composition of the present invention comprises, based on the overall weight of the composition, between about 5 precent and about 30 percent, and preferably from about percent to about 15 percent of alcohol.

The third component of the composition of the present invention is a surfactant, which includes any type of surfactant known in the art such as anionic, cationic, amphoteric or nonionic surfactants. Nonionic surfactants are preferred. The nonionic surfactant is preferably selected from alkoxylated alcohols, alkoxylated alkyl phenols, alkoxylated acids, alkoxylated amides, alkoxylated amines, alkoxylated sugar derivatives, alkoxylated derivatives of natural oils or waxes, polyoxyethylene polyoxypropylene block copolymers or mixtures thereof, wherein said alkoxylated surfactants are alkoxylated with ethylene oxide or propylene oxide, with ethylene oxide being preferred.

Exemplary alkoxylated alcohols useful as the nonionic surfactant in the compositions of the invention have the structure shown in formula II below:

II wherein $R_5$ is a branched or unbranched alkyl group having from about 6 to about 22 carbon atoms and y is between about 4 and about 100, and preferably, between about 10 and about 100. A preferred surfactant of this class of materials is the species wherein $R_5$ is a lauryl group and y has an average value of 23. This surfactant is known by the CTFA name "laureth 23" and is available from ICI Americas, Inc. of Wilmington, Del. under the tradename, "BRIJ 35."

Another exemplary alkoxylated alcohol surfactant/ emulsifier is an ethoxylated derivative of lanolin alcohol. Lanolin alcohol is a mixture of organic alcohols obtained from the hydrolysis of lanolin. An example of an ethoxylated derivative of lanolin alcohol is laneth-10, which is the polyethylene glycol ether of lanolin alcohol with an average ethoxylation value of 10.

Another exemplary alkoxylated alcohol surfactant/ emulsifier is polyoxypropylene polyoxyethylene alkyl ether, the structure of which is shown schematically in formula VII below:

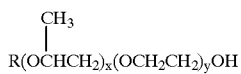
VII wherein x:y is about 2:2 to about 38:37. An exemplary member of this class of materials is the material known by the CTFA name "PPG-12-Buteth-16," which conforms to structure VII above wherein R is a butyl group, x has an average value of 12 and y has an average value of 16. This material is available from Amerchol Corp. of Edison, N.J. under the tradename, "UCON Fluid 50-HB-660."

Another class of surfactants useful in the compositions of the invention are the alkoxylated alkyl phenols, which generally conform to the structure:

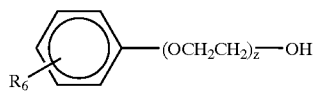
III wherein $R_6$ is a branched or unbranched alkyl group having about 6 to about 22 carbon atoms and z is between about 7 and 120, and preferably, between about 10 and about 120. An especially preferred member of this class of materials is the species wherein $R_6$ is a nonyl group and z has an average value of about 14. This material is known by the CTFA name "nonoxynol-14" and is available under the tradename, "MAKON 14" from the Stepan Company of Northfield, Ill.

Another class of surfactants useful in the compositions of the invention are the alkoxylated acids, which are esters of an acid, most usually a fatty acid, with a polyalkylene glycol. An exemplary material of this class has the CTFA name "PEG-8 laurate," and the following structure shown in formula VIII:

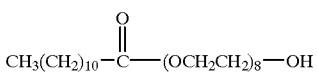
VIII

Another class of surfactants useful in the compositions of the invention are the alkoxylated amides that may conform to one or both of structures IX or X shown below:

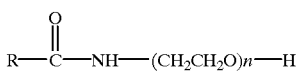
IX

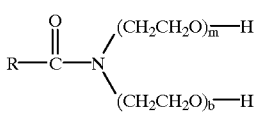
X wherein n is from about 8 to about 100 and the sum of m plus b is from about 8 to about 100. An exemplary member of this class is known by the CTFA name "PEG-6 Cocoamide," which conforms generally to structure IX wherein RCO represents the fatty acids derived from coconut oil and n has an average value of about 6.

Another class of surfactants useful in the compositions of the invention are the alkoxylated sugar derivatives. An exemplary member of this class, which is known by the CTFA name "Polysorbate 20," is a mixture of laurate esters of sorbitol and sorbitol anhydrides, consisting predominately of the monoester, condensed with about 20 moles of ethylene oxide. This material is available under the tradename "TWEEN 20" from ICI Americas of Wilmington, Del.

Another example of an alkoxylated sugar derivative useful in the compositions of the invention is PEG-20 methylglucose sesquistearate, which is the polyethyleneglycol ether of the sesquiester of methyl glucose and stearic acid, contains an average of 20 moles of ethylene oxide, and is available under the tradename, "Glucamate SSE-20" from the Amerchol Corp. of Edison, N.J.

Another class of surfactants useful in the compositions of the invention are the alkoxylated derivatives of natural oils and waxes. Examples of this class of material include PEG40 lanolin, PEG40 castor oil and PEG-40 hydrogenated castor oil.

Another class of surfactants useful in the compositions of the invention are the polyoxyethylene polyoxypropylene block copolymers. These materials are generally known by the CTFA name, "Poloxamer" and conform to the structure:

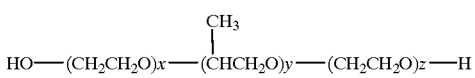
XI wherein x:y:z is from about 2:16:2 to about 98:67:98. Exemplary members of this class of materials useful in the compositions of the invention are "Poloxamer 101" and "Poloxamer 182," in which x, y and z have average values of 2, 16 and 2 and 8, 30 and 8, respectively.

Preferred nonionic surfactants include the alkoxylated alcohols and the alkoxylated alkyl phenols, with laureth-23 being more preferred.

The composition of the present invention comprise, based upon the total weight of the composition, from about 1 percent to about 10 percent, preferably from about 1 percent to about 7.5 percent, and more preferably from about 3 percent to about 6 percent of surfactant.

The compositions of the invention may also contain other optional additives known in the art of personal care product formulations, such as thickeners, buffering agents, chelating agents, preservatives, fragrances, and mixtures thereof.

Preferred thickeners are the homopolymers or copolymers of acrylic acid or salts thereof. An exemplary thickener useful in the compositions of the invention is the material known by the CTFA name, "Acrylates/C10–30 Alkyl Acrylate Crosspolymer," which is a copolymer of C10–30 alkyl acrylates and one or more monomers of acrylic acid, methacrylic acid or one of their simple esters crosslinked with an allyl ether of sucrose or an allyl ether of pentaerythritol. One such material useful in the compositions of the invention is marketed by BFGoodrich Specialty Chemicals of Cleveland, Ohio under the tradename, "CARBOPOL ETD 2020." Another useful thickener includes the material known by its CTFA name, "Carbomer," which is a crosslinked homopolymer of acrylic acid.

In use, the thickener polymers are preferably neutralized with an inorganic or organic base. Exemplary inorganic bases include sodium hydroxide and potassium hydroxide. Exemplary organic bases include triethanolamine and tris (hydroxymethyl)amino methane, that latter of which is known by the CTFA name, "tromethamine."

If it is desired to deliver the composition in the form of a thickened liquid or gel, the composition preferably has a viscosity of about 100 to about 30,000 centipoise, and more preferably from about 10,000 to about 20,000 centipoise.

Buffering agents known in the art are preferably present in the composition of the present invention to maintain its pH in the range of about 5.5 to about 7.5.

The compositions of the present invention may also contain one or more therapeutically or cosmetically active ingredients. Exemplary therapeutic or cosmetically active ingredients useful in the compositions of the invention include fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents or antihistamines, and may be present in an amount effective for achieving the therapeutic or cosmetic result desired.

The compositions of the invention may be formulated and packaged so as to deliver the product in a variety of forms including, but not limited to, a cologne, a lotion, a spray, an aerosol, a cream, a milk, a gel, an ointment, a suspension, a dispersion, a foam, a makeup, a shampoo, a hair lacquer or a hair rinse. The compositions of the invention are also preferably optically transparent.

The method of applying the insect repellant composition will depend upon its form as enumerated above. For example, when the composition is in the form of a lotion, the composition could be dispensed on the hands or on other body parts of the host, and then uniformly spread over a larger portion of the body. In the case of an aerosol or spray, the composition may be applied as such and either left on or further spread over parts of the body. For application to the hair or scalp, the compositions may be applied either as a leave-on or as a rinse-off type product.

Another embodiment of the present invention is directed to a method of reducing the rate of degradation of the insect repellant active materials in aqueous solution. We have unexpectedly discovered that by combining under conditions sufficient the insect repellant active materials with a degradation-reducing amount of the surfactants, and preferably the non-ionic surfactants, of the composition of the present invention, the degradation rate of the insect repellant active materials was significantly reduced.

Preferred degradation reducing surfactants include the alkoxylated alcohols and alkoxylated alkyl phenols of the types and in the amounts enumerated above, with laureth-23 and nonoxynol-14 being most preferred.

As used herein, "degradation reducing" amount means the amount of surfactant such that the decomposition of the insect repellant active material in the presence of the surfactant is at least about 5%, preferably at least about 10%, and more preferably at least about 15% less than the amount of insect repellant active material that would have been degraded in the absence of the surfactant, with comparable time, temperature, and pressure conditions. For example, in a surfactant-free composition containing 100 parts of insect repellant active material, 10 parts of the material would have degraded under certain conditions. By contrast, when surfactant is added to the same insect repellant active material-containing composition in the relevant concentrations, then the degradation amount of surfactant in the composition would be the amount that would retard the degradation of the insect repellant active material to no more than 9.5 parts, or preferably 9 parts, or more preferably 8.5 parts. Typically, the degradation reducing amount of nonionic surfactant is, based upon the total weight of the composition, of from about 1 percent to about 10 percent and preferably, from about 1 percent to about 7.5 percent. Preferably the surfactant, the active material, and other ingredients are combined under ambient conditions.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Insect Repellant Formulation

Into a stirred vessel the ingredients set forth in Table 1 below were added in sequence and stirred until the mixture was homogeneous:

TABLE 1

| Component/Supplier | Concentration (weight %) | |
|---|---|---|
| | Ex. 1 | Comparative Example 1 |
| ethyl 3-(N-butyl-acetamido) propionate from Merck KgaA under the name, "Insect Repellent 3535" | 12.5 | 12.5 |
| 1,3-butylene glycol | 12.5 | 12.5 |
| laureth-23 from ICI Americas, Inc. under the name, "BRIJ 35" | 5.0 | 0 |
| water | q.s. to 100% | q.s. to 100% |

Comparative Example 1

Preparation of Surfactant-Free Insect Repellant Formulation

The composition of Comparative Example 1 was prepared in accordance with the procedure set forth in Example 1, except that the laureth-23 surfactant was omitted therefrom as shown in Table 1 above.

The active ingredient, ethyl 3-(N-butylacetamido) propionate, when undergoing degradation in aqueous solution was expected to undergo hydrolysis according to the following equation:

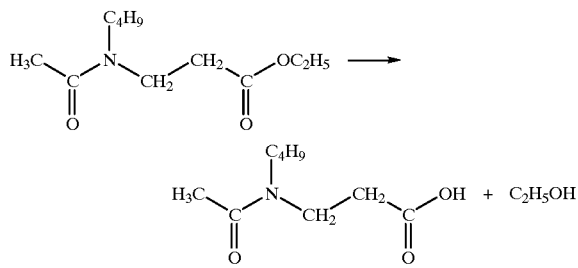

Since the hydrolysis product of this active ingredient is an acid, i.e., 3-(N-butylacetamido) propionic acid, its hydrolytic degradation was expected to be accompanied by a shift to lower pH. Table 2 shows the change in pH of the composition of Example 1 over time as compared with the pH changes of the surfactant-free composition of Comparative Example 1.

TABLE 2

| | pH | |
|---|---|---|
| Days at room temperature | Example 1 | Comparative Example 1 |
| 0 | 4.5 | 4.5 |
| 5 | 4.4 | 4.2 |
| 10 | 4.2 | 3.9 |
| 15 | 4.1 | 3.6 |
| 20 | 4.1 | 3.6 |
| 25 | 4.0 | 3.5 |

This Example shows that the surfactant-containing composition of Example 1 did not decrease in pH to the same extent as the surfactant-free composition of Comparative Example 1, which thereby suggests that the nonionic surfactant contributes to the reduction in the degradation of the insect repellant active material in aqueous solution.

Examples 2–4 and Comparative Example 2

Preparation of Additional Surfactant-Containing and Surfactant-free Compositions The formulations shown in Table 3 were prepared in accordance with the manner described in Example 1. The changes in pH stability of these formulations with time are shown in Table 4.

TABLE 3

| | Component Concentration (weight %) | | | |
|---|---|---|---|---|
| Component | Example 2 | Example 3 | Example 4 | Comparative Example 2 |
| ethyl 3-(N-butyl-acetamido) propionate | 20 | 20 | 20 | 20 |

TABLE 3-continued

| | Component Concentration (weight %) | | | |
|---|---|---|---|---|
| Component | Example 2 | Example 3 | Example 4 | Comparative Example 2 |
| 1,3-butylene glycol | 20 | 20 | 20 | 20 |
| laureth-23 | 3.5 | 5 | 7.5 | 0 |
| water | q.s. to 100% | q.s. to 100% | q.s. to 100% | q.s. to 100% |

TABLE 4

| | pH | | | |
|---|---|---|---|---|
| Weeks @ 50° C. | Example 2 | Example 3 | Example 4 | Comparative Example 2 |
| 0 | 4.5 | 4.7 | 4.7 | 4.4 |
| 1 | 4.1 | 4.3 | 4.6 | 3.8 |
| 2 | 4.1 | 4.1 | 4.5 | 3.7 |
| 3 | 3.7 | 4.0 | 4.2 | 3.3 |
| 4 | 3.4 | 3.7 | 4.0 | 3.2 |
| 5 | 3.4 | 3.5 | 3.9 | 3.1 |

These Examples show that the formulations containing the nonionic surfactant have a reduced pH drift relative to the surfactant-free formulation. Furthermore, the rate of pH drift, which is indicative of the rate of hydrolysis, decreases as the amount of surfactant in the formulation increases. This Example therefore further supports our belief that the greater the amount of nonionic surfactant present in the composition, the lower the degradation rate of insect repellant active material.

Example 5

Measure of Insect Repellent Active Material Degradation

The degradation of the active material ethyl 3-(N-butylacetamido) propionate contained in the formulations of Example 4 and Comparative Example 2, respectively, was measured directly by liquid chromatography. Approximately 10 $\mu$l of each formulation was placed in an endcapped LiChroCART stainless steel column available from EM Sciences of Gibbstown, N.J. (catalog No. 50995), having a 250 mm length by 4 mm diameter and containing Lichrospher 100 RP-18 packing material having a film thickness of 5 $\mu$m. The analytical procedure used an isocratic mobile phase of acetonitrile/water (31:69) at a flow rate of 1.0 mL/min on a liquid chromatograph equipped with a 220 nm UV detector. The results are shown in Table 8.

TABLE 8

| | Analytically determined percent actives in formulation (percent degradation) | |
|---|---|---|
| Time @ 50° C. (weeks) | Example 4 | Comparative Example 2 |
| 0 | 21.6 | 21.8 |
| 3 | 20.4 (5.5) | 18.3 (16.1) |
| 6 | 20.6 (4.6) | 17.8 (18.3) |

This Example shows that the formulation of Example 4 containing 7.5% laureth-23 showed less degradation that the surfactant-free formulation of Comparative Example 2, which further supports our belief that the selected nonionic surfactants contribute to the reduction in degradation of the active insect repellent material.

Examples 6–8 and Comparative Example 3

Preparation of Additional Surfactant-Containing Compositions and Surfactant-Free Compositions The formulations shown in Table 2 were prepared in accordance with the manner described in Example 1, but the laureth-23 surfactant was replaced by nonoxynol-14 available from the Stepan Company under the tradename, "MAKON 14." The compositions of these formulations are shown in Table 5 and the pH stability of these formulations is shown in Table 6.

TABLE 5

| | Component Concentration (Weight %) | | | |
|---|---|---|---|---|
| Component | Example 6 | Example 7 | Example 8 | Comparative Example 3 |
| ethyl 3-(N-butyl-acetamido) propionate | 20 | 20 | 20 | 20 |
| 1,3-butylene glycol | 20 | 20 | 20 | 20 |
| Nonoxynol-14 | 3.5 | 5 | 7.5 | 0 |
| water | q.s. to 100% | q.s. to 100% | q.s. to 100% | q.s. to 100% |

TABLE 6

| | pH | | | |
|---|---|---|---|---|
| Time @ 50° C. (weeks) | Example 6 | Example 7 | Example 8 | Comparative Example 3 |
| 0 | 5.12 | 5.27 | 5.5 | 4.46 |
| 1 | 4.57 | 4.87 | 5.21 | 3.81 |
| 2 | 4.87 | 4.51 | 4.92 | 3.51 |
| 4 | 3.7 | 4.07 | 4.49 | 3.25 |
| 5 | 3.55 | 3.82 | 4.31 | 3.11 |

These Examples show that the formulations containing the nonoxynol-14 nonionic surfactant do not decrease in pH to the value of the corresponding surfactant-free formulation. Similarly, the rate of pH drift, indicative of the rate of hydrolysis, also decreases with increasing quantities of surfactant in the formulation.

Example 9 and Comparative Example 4

Thickener-Containing and Thickener-Free Compositions 2.0 parts laureth-23 were dissolved in 54.3 parts water to form Premix A. Premix B was then formed by adding 12.5 parts butylene glycol to 12.5 parts ethyl 3-(N-butylacetamido) propionate. Premix A was then added with stirring to Premix B until the mixture was homogeneous to form Premix C.

0.25 parts of a crosslinked Acrylate/C10–30 Alkyl Acrylate Crosspolymer marketed by BFGoodrich Specialty Chemicals of Cleveland, Ohio as a under the tradename, "Carbopol ETD 2020" were added with stirring into a vessel containing 18.1 parts water until a uniform mucilage was formed. After neutralizing the mucilage by adding triethanolamine thereto with stirring until a clear gel was formed, the resulting mucilage was added with stirring into a vessel containing Premix C until a uniform gel was obtained.

The composition of Comparative Example 4 was made according to the procedure of Example 1.

The compositions of the resulting formulations are shown in Table 7:

TABLE 7

| | Component Concentration (Weight %) | |
|---|---|---|
| Component | Example 9 | Comparative Example 4 |
| ethyl 3-(N-butylacetamido) propionate | 12.5 | 12.5 |
| 1,3-butylene glycol | 12.5 | 12.5 |
| laureth-23 | 2.0 | 2.0 |
| Acrylate/C10–30 Alkyl Acrylate Crosspolymer | 0.25 | 0 |
| triethanolamine | 0.35 | 0 |
| water | q.s. to 100% | q.s. to 100% |

The formulation of Example 9 has a viscosity of about 8000 to about 10000 centipoise. The rate of change of the pH of these formulations as a function of time upon storage at a temperature of 50° C. is shown in FIG. 1.

These Examples show that the thickener-containing formulation of Example 8 has a lower rate of pH change, and hence, a lower implied rate of degradation of the active material, than the thickener-free formulation of Comparative Example 4.

Examples 10–13

Insect Repellent Efficacy

The formulations shown in Table 9 were prepared in the manner described in Example 1.

TABLE 9

| | Component Concentration (weight %) | | | |
|---|---|---|---|---|
| Component | Example 10 | Example 11 | Example 12 | Example 13 |
| ethyl 3-(N-butyl-acetamido) propionate | 12.5 | 12.5 | 12.5 | 12.5 |
| 1,3-butylene glycol | 12.5 | 12.5 | 12.5 | 12.5 |
| laureth-23 | 0 | 1.5 | 3.0 | 5.0 |
| water | q.s. to 100% | q.s. to 100% | q.s. to 100% | q.s. to 100% |

After applying 0.7 grams of each formulation in Examples 10–13, respectively, to the forearms of three male subjects, the subjects then inserted their forearms into 25 cm×25 cm×40 cm cheesecloth-covered wire cages containing approximately 500 seven-to-ten-day-old mixed sex *Aedes aegypti* mosquitoes. Assessments were conducted for three minutes per arm commencing immediately after the application of the formulation thereto and every hour thereafter until a confirmed bite was recorded. A confirmed bite was defined as more than one bite in a given exposure period or one bite in each of two consecutive exposure periods.

A 15 second pre-treatment exposure of an untreated forearm was conducted for each subject at the beginning of each day of testing. Greater than 10 landings and bites were recorded in this period for each subject.

The data were analyzed using two-way analysis of variance with treatment means separated using least significant difference techniques. The repellency data for the formulations of Table 9 are shown in Table 10.

TABLE 10

| Composition of Example | Subject # | Bites in Treatment Hour | | | | | | Con-firmed Bite Hour | Mean Efficacy (hours) |
|---|---|---|---|---|---|---|---|---|---|
| | | 0 | 1 | 2 | 3 | 4 | 5 | | |
| 10 | 1 | 0 | 0 | 0 | 2 | | | 3 | |
| 10 | 2 | 0 | 0 | 0 | 3 | | | 3 | 3 |
| 10 | 3 | 0 | 0 | 0 | 1 | 3 | | 3 | |
| 11 | 1 | 0 | 0 | 1 | 3 | | | 2 | |
| 11 | 2 | 0 | 0 | 0 | 0 | 2 | | 4 | 3.7 |
| 11 | 3 | 0 | 0 | 0 | 0 | 0 | 3 | 5 | |
| 12 | 1 | 0 | 0 | 0 | 0 | 0 | 5 | 5 | |
| 12 | 2 | 0 | 0 | 0 | 0 | 2 | | 4 | 4.3 |
| 12 | 3 | 0 | 0 | 0 | 0 | 5 | | 4 | |
| 13 | 1 | 0 | 0 | 3 | | | | 2 | |
| 13 | 2 | 0 | 0 | 0 | 0 | 4 | | 4 | 3.3 |
| 13 | 3 | 0 | 0 | 0 | 0 | 3 | | 4 | |

Due to the limited sample size, the least significant difference in mean efficacy that would be statistically significant at the 95% confidence level would be a difference of 2 hours. While none of the data for Examples 10–13 are different at this level of statistical significance, the data do point to a trend in increasing efficacy with the addition of surfactant, which we believe could be confirmed with larger sample sizes. Further analysis of the data indicate that the examples with surfactant (Examples 11–13) are statistically different from the sample without surfactant (Example 10) at the 70% confidence level.

Examples 14–16

Particle Size Analysis of the Formulations

The formulations shown in Table 11 were prepared in the manner described in Example 1.

TABLE 11

| | Component Concentration (weight %) | | |
|---|---|---|---|
| Component | Example 14 | Example 15 | Example 16 |
| ethyl 3-(N-butylacetamido) propionate | 12.5 | 12.5 | 12.5 |
| 1,3-butylene glycol | 12.5 | 12.5 | 12.5 |
| laureth-23 | 0 | 3.5 | 5.0 |
| water | q.s. to 100% | q.s. to 100% | q.s. to 100% |
| Number Weighted Distribution (nm) | 9.6 ± 2.0 (100%) | 11.5 ± 2.4 (100%) | 4.3 ± 0.5 (100%) |

All of these formulations were optically transparent. The particle sizes of the resultant formulations were analyzed by exposing each formulation to dynamic laser light scattering using a NICOMP 370 submicron particle analyzer available from Particle Sizing Systems, Inc. of Santa Barbara, Calif. The number-weighted mean diameter of the particles in the compositions of Examples 14–16 are also recorded in Table 11.

The compositions of Examples 14–16 were also examined using freeze-fracture transmission electron microscopy (TEM). Samples of the compositions were prepared in accordance with techniques described in chapter 5 of "Low Temperature Microscopy and Analysis" by Patrick Echlin, Plenum Publishing Corp., New York, 1992, which is incorporation herein by reference, except that the samples were rapidly cooled with liquid propane to −196° C. and, after fracturing, were etched at −150° C. to remove a surface layer of water. Freeze fracture photomicrographs at 150,000× of the resulting specimens prepared from the compositions of Examples 14, 15 and 16 are shown in FIGS. 2, 3 and 4, respectively.

Figure 2:
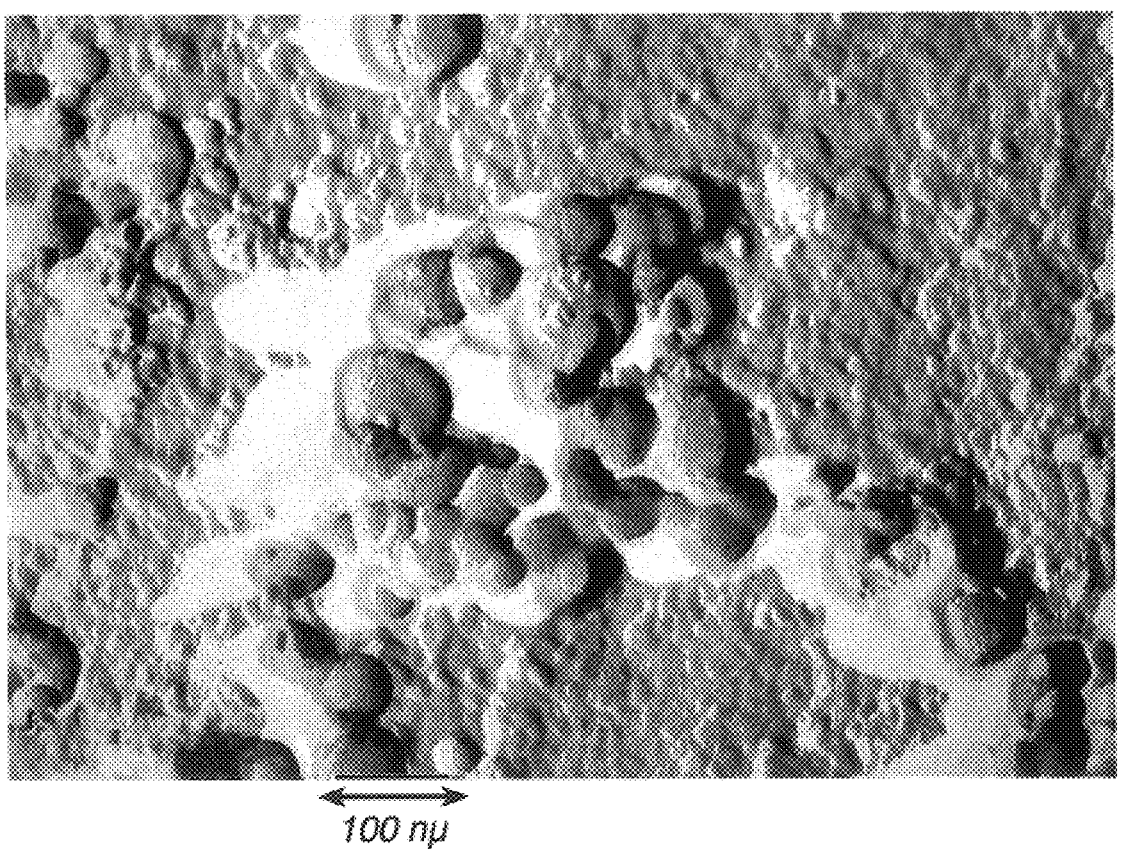
FIG. 2 is a freeze-fracture transmission electron photomicrograph at a magnification of 150,000× of an aqueous surfactant-free composition containing an insect repellant active material.

The photomicrograph of FIG. 2, which was taken of the specimen prepared from the surfactant-free composition of Example 14, shows the presence of large agglomerates ranging in size from about 50 to about 150 nm. These agglomerates are suggestive of unsolubilized insect repellant active material and are expected to be unstable on product storage.

Figure 3:
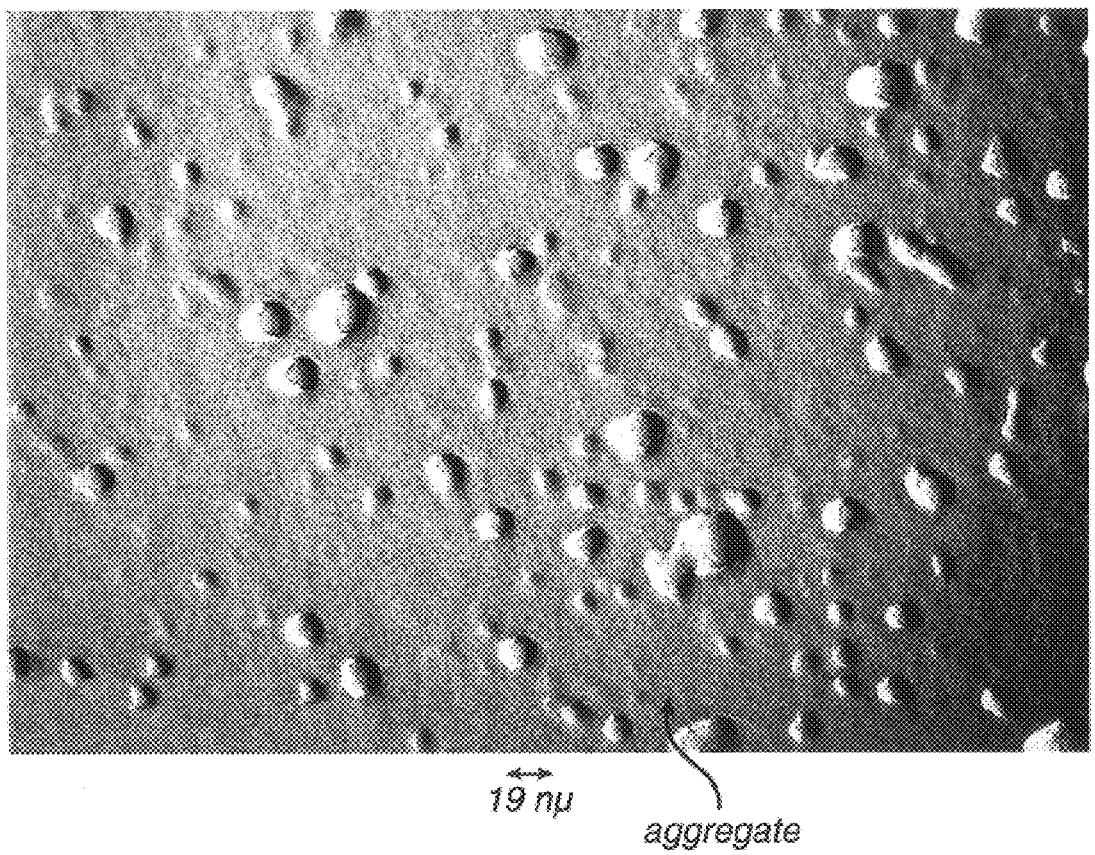
FIG. 3 is a freeze-fracture transmission electron photomicrograph at a magnification of 150,000× of an insect repellant composition of the present invention containing 3.5% laureth-23 surfactant.

The photomicrograph of FIG. 3, which was taken of the specimen prepared from the 3.5% laureth-23-containing composition of Example 15, shows some degree of agglomeration; however, the amount is greatly reduced relative to the amount of agglomeration in the composition of Example 14. This photomicrograph also shows the presence of ordered structures which are believed to be micelles or vesicles ranging in size from about 13 to about 25 nm.

Figure 4:
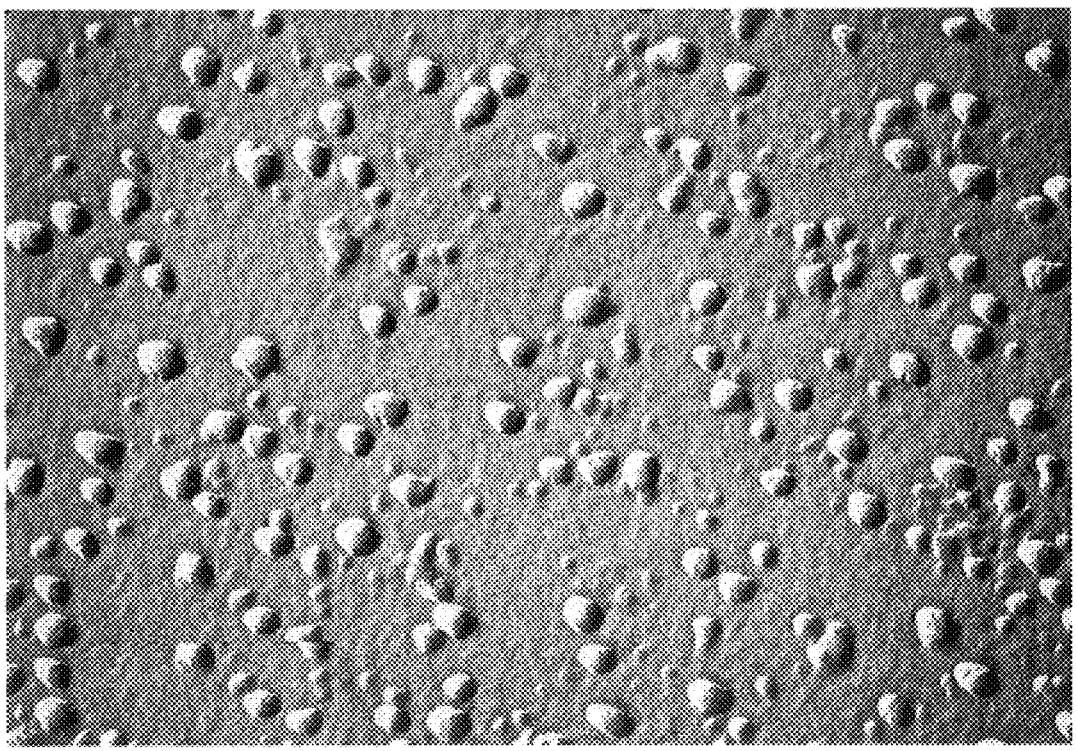
FIG. 4 is another freeze-fracture transmission electron photomicrograph at a magnification of 150,000× of an insect repellant composition of the present invention containing 5.0% laureth-23 surfactant.

The photomicrograph of FIG. 4, which was taken of the specimen prepared from the 5% laureth-23-containing composition of Example 16, shows no large agglomerates. This Example shows that the presence of more surfactant in the formulation of Example 15 also gives rise to a greater number of smaller, more uniform micelles of spherical shape than those of Example 15, and thus a more stable formulation.

While not intending to be bound by the following theory, it is believed that the preferred formulations of the present invention exhibit increased stability against degradation of the insect repellant active material because the active material is contained, at least in part, within the ordered micellar structures seen in the photomicrographs of FIGS. 3 and 4. The micelles are believed to protect the active material from degradation by the aqueous environment.

Example 17

Preparation of Formulation Containing Buffering Agent and Chelating Agent 0.68 parts of disodium hydrogen phosphate and 0.87 parts potassium dihydrogen phosphate were dissolved in 68.15 parts deionized water. 0.05 parts VERSENE NA disodium ethylenediamine tetraacetic acid (EDTA) was added with stirring thereto until it fully dissolved to form Premix A.

In a separate vessel, the following ingredients were charged in succession with constant agitation: 12.5 parts ethyl 3-(N-butylacetamido) propionate; 12.5 parts 1,3-butylene glycol; 0.25 parts fragrance; 5.0 parts laureth-23; and Premix A in order to form an insect repellant formulation.

Examples 18–22

Preparation of Insect Repellent Cologne

Examples 18–22 are prepared according to the method of Example 17 using the components set forth in Table 12:

TABLE 12

| | Component Concentration (weight %) | | | | |
|---|---|---|---|---|---|
| Component | Example 18 | Example 19 | Example 20 | Example 21 | Example 22 |
| ethyl 3-(N-butylacetamido) propionate | 12.5 | 12.5 | 12.5 | | 12.5 |
| DEET | | | | 6.0 | |
| Ethanol | | | | | 10.0 |
| 1,3-propylene glycol | | 12.5 | | | 12.5 |

TABLE 12-continued

| Component | Component Concentration (weight %) | | | | |
|---|---|---|---|---|---|
| | Example 18 | Example 19 | Example 20 | Example 21 | Example 22 |
| 1,3-butylene glycol | | | 6.25 | 5.0 | |
| pentylene glycol | | 12.5 | 6.25 | | |
| laureth-23 | 3.5 | 3.5 | 3.5 | | 5.0 |
| Laureth 12 | | | | | 5.0 |
| Nonoxynol-14 | | | | 5.0 | |
| fragrance | 0.25 | 0.25 | 0.25 | 0.25 | 0.25 |
| water | q.s. to 100% | q.s. to 100% | q.s. to 100% | q.s. to 100% | q.s. to 100% |

The resulting formulations are useful as an insect repellant cologne.

Examples 23 and 24

Preparation of Insect Repellant Gels and Sprays

The formulations of Examples 23 and 24 are prepared according to the method of Example 9 but with the components set forth in Table 13:

TABLE 13

| | Component Concentration (weight percent) | |
|---|---|---|
| Component | Example 23 | Example 24 |
| ethyl 3-(N-butylacetamido) propionate | 12.5 | 12.5 |
| Butylene Glycol | 12.5 | 12.5 |
| polyvinyl pyrrolidone | 5.0 | 5.00 |
| Laureth-23 | 3.0 | 2.00 |
| Carbomer * | | 1.00 |
| Triethanolamine | | 1.00 |
| Purified Water | q.s. to 100% | q.s. to 100% |

* available from Goldschmidt Chemical Corp. of Hopewell, VA.

The resulting compositions are useful as a lice repellant hair spray and hair gel, respectively.

Example 25

Preparation of Insect Repellant Compositions

The formulation of Example 25 is prepared according to the method of Example 9, but with the components set forth in Table 14:

TABLE 14

| Component | Component Concentration (weight percent) Example 25 |
|---|---|
| Triclosan* | 0.25 |
| ethyl 3-(N-butylacetamido) propionate | 12.50 |
| Butylene Glycol | 12.50 |
| nonoxynol 14 | 7.00 |
| Carbomer | 0.25 |

TABLE 14-continued

| Component | Component Concentration (weight percent) Example 25 |
|---|---|
| Triethanolamine | 0.35 |
| Purified Water | q.s. |

*available from Ciba Specialty Chemicals Corp. of Greensboro, NC

The resulting composition is useful as an antibacterial insect repellant.

We claim:

1. An insect repellant composition comprising, based upon the total weight of the composition:
from about 6 to about 30 percent of an insect repellant active material consisting essentially of at least one material selected from the group consisting of:
one or more compounds of the formula

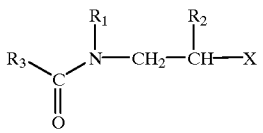

wherein
$R_1$ is a branched or unbranched alkyl group having about 1 carbon atom to about 6 carbon atoms;
$R_2$ is H, methyl or ethyl;
$R_3$ is a branched or unbranched alkyl or alkoxy group having from about 1 carbon atom to about 8 carbon atoms; and
X is a —CN or a —COOR$_4$ group, wherein
$R_4$ is a branched or unbranched alkyl group having from about 1 carbon atom to about 6 carbon atoms;
from about 5 to about 30 percent of alcohol selected from the group consisting of:
a glycol monoalkyl ether, said alkyl having from about 1 carbon atom to about 4 carbon atoms;
a glycol containing from about 3 carbon atoms to about 6 carbon atoms;
oligomers of ethylene glycol or propylene glycol; and
mixtures thereof; and
from about 1 to about 10 percent of surfactant selected from the group consisting of:
alkoxylated alcohols having the structure

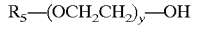

wherein $R_5$ is a branched or unbranched alkyl group having about 6 carbon atoms to about 22 carbon atoms and y is between about 10 and about 100;
alkoxylated alkyl phenols having the structure

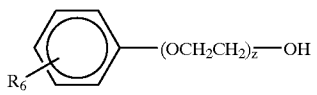

wherein $R_6$ is a branched or unbranched alkyl group having about 6 carbon atoms to about 22 carbon atoms and z is between about 10 and about 120; and mixtures thereof, wherein the composition contains less than about 5% by weight of lower monohydric alcohols having from about 2 to about 4 carbon atoms.

2. The composition of claim 1, wherein the insect repellent active material is ethyl 3-(N-butylacetamido) propionate.

3. The composition of claim 1 wherein the alcohol is a glycol selected from the group consisting of propylene glycol, butylene glycol, pentylene glycol, hexylene glycol, oligomers of ethylene glycol, oligomers of propylene glycol and mixtures thereof.

4. The composition of claim 1 which further comprises one or more additives selected from the group consisting of thickeners, buffering agents, chelating agents, and fragrances.

5. The composition of claim 4 wherein the composition further comprises a thickener, said thickener being selected from the group consisting of an acrylic acid homopolymer or a salt thereof, a copolymer of acrylic acid or a salt thereof, and mixtures thereof.

6. The composition of claim 1 which further comprises one or more therapeutically or cosmetically active ingredients selected from the group consisting of fungicides, sunscreening agents, sunblocking agents, vitamins, tanning agents, plant extracts, anti-inflammatory agents, antioxidants, radical scavenging agents, retinoids, alpha-hydroxy acids, emollients, antiseptics, antibiotics, antibacterial agents and antihistamines.

7. The composition of claim 1 which has a pH in the range of about 5.5 to about 7.5.

8. The composition of claim 1 wherein the surfactant is laureth-23.

9. The composition of claim 1 wherein the composition is in the form of a cologne, a lotion, a spray, an aerosol, a cream, a milk, a gel, an ointment, a suspension, a dispersion, a foam, a makeup, a shampoo, a hair lacquer or a hair rinse.

10. The insect repellant composition according to claim 1, wherein said composition is comprised of ordered structures selected from micelles, vesicles or mixtures thereof.

11. The composition of claim 10 wherein the number-weighted mean diameter of the ordered structures is less than about 100 nanometers.

12. The composition of claim 10 wherein the number-weighted mean diameter of the ordered structures is less than about 5 nanometers.

13. The composition of claim 1 which comprises, based upon the total weight of the composition, from about 10 to about 15 percent of said insect repellent active material, about 10 to about 15 percent of said alcohol and about 1 to about 7.5 percent of said surfactant.

14. The composition of claim 1 wherein
the insect repellant active material is ethyl 3-(N-butylacetamido)propionate;
the alcohol is a glycol selected from propylene glycol, butylene glycol, pentylene glycol, hexylene glycol, oligomers of ethylene glycol, oligomers of propylene glycol or mixtures thereof; and,
the surfactant is selected from alkoxylated alcohols having the structure

$R_5$—(OCH$_2$CH$_2$)$_y$—OH wherein $R_5$ is a branched or unbranched alkyl group having about 6 carbon atoms to about 22 carbon atoms and y is between about 10 and about 100;

alkoxylated alkyl phenols having the structure

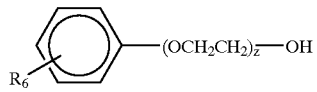

wherein $R_6$ is a branched or unbranched alkyl group having about 6 carbon atoms to about 22 carbon atoms and z is between about 10 and about 120; or mixtures thereof, wherein said repellant composition contains less than about 5% by weight of lower monohydric alcohols having from about 2 to about 4 carbon atoms.

15. The composition of claim 14 which comprises, based on the total weight of the composition, about 10 percent to about 15 percent of said insect repellant active material, about 10 percent to about 15 percent of said glycol and about 1 percent to about 7.5 percent of said surfactant.

16. A method of reducing the rate of degradation of an insect repellant active material in an insect repellant composition wherein said insect repellant active material is present at from about 6 to 30 percent of the composition and consists essentially of a material selected from the group consisting of
one or more compounds of the formula

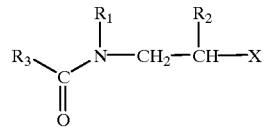

wherein
$R_1$ is a branched or unbranched alkyl group having about 1 carbon atom to about 6 carbon atoms;
$R_2$ is H, methyl or ethyl;
$R_3$ is a branched or unbranched alkyl or alkoxy group having from about 1 carbon atom to about 8 carbon atoms; and
X is a —CN or a —COOR$_4$ group, wherein
$R_4$ is a branched or unbranched alkyl group having from about 1 carbon atom to about 6 carbon atoms;

comprising the step of incorporating into the composition a degradation-effective amount of a surfactant selected from the group consisting of alkoxylated alcohols having the structure

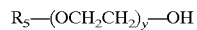
$R_5$—(OCH$_2$CH$_2$)$_y$—OH wherein $R_5$ is a branched or unbranched alkyl group having about 6 carbon atoms to about 22 carbon atoms and y is between about 10 and about 100;
alkoxylated alkyl phenols having the structure

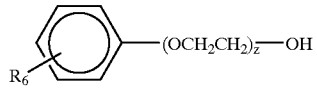

wherein $R_6$ is a branched or unbranched alkyl group having about 6 carbon atoms to about 22 carbon atoms and z is between about 10 and about 120; and mixtures thereof, wherein said repellant composition contains less than about 5% by weight of lower monohydric alcohols having from about 2 to about 4 carbon atoms.

17. The method of claim 16, wherein said insect repellant composition comprises, from about 10 percent to about 15 percent of said insect repellant active material which is selected from the group consisting of compounds of the formula

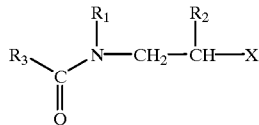

wherein
$R_1$ is a branched or unbranched alkyl group having about 1 carbon atom to about 6 carbon atoms;
$R_2$ is H, methyl or ethyl;
$R_3$ is a branched or unbranched alkyl or alkoxy group having from about 1 carbon atom to about 8 carbon atoms;
X is a —CN or a —COOR$_4$ group; wherein
$R_4$ is a branched or unbranched alkyl group having from about 1 carbon atom to about 6 carbon atoms and mixtures thereof; and
from about 1 percent to about 7.5 percent of said surfactant.

18. A method of repelling insects from a host comprising topically applying to the host an insect repellant composition, said composition comprising:

from about 6 to about 30 percent of insect repellant active material selected from the group consisting of one or more compounds of the formula

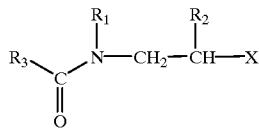

wherein
$R_1$ is a branched or unbranched alkyl group having about 1 carbon atom to about 6 carbon atoms;
$R_2$ is H, methyl or ethyl;
$R_3$ is a branched or unbranched alkyl or alkoxy group having from about 1 carbon atom to about 8 carbon atoms; and
X is a —CN or a —COOR$_4$ group, wherein
$R_4$ is a branched or unbranched alkyl group having from about 1 carbon atom to about 6 carbon atoms;

from about 5 to about 30 percent of alcohol selected from
a glycol monoalkyl ether, said alkyl having from about 1 carbon atom to about 4 carbon atoms;
a glycol containing from about 3 carbon atoms to about 6 carbon atoms;
oligomers of ethylene glycol or propylene glycol; or mixtures thereof; and from about 1 to about 10 percent by weight of surfactant selected from the group consisting of alkoxylated alcohols having the structure

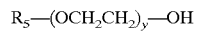

wherein $R_5$ is a branched or unbranched alkyl group having about 6 carbon atoms to about 22 carbon atoms and y is between about 10 and about 100;
alkoxylated alkyl phenols having the structure

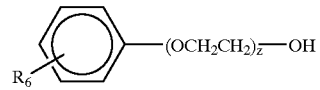

wherein $R_6$ is a branched or unbranched alkyl group having about 6 carbon atoms to about 22 carbon atoms and z is between about 10 and about 120; and mixtures thereof, wherein the composition contains less than about 5% by weight of lower monohydric alcohols having from about 2 to about 4 carbon atoms.

19. The method of claim 18 wherein the alcohol is a glycol selected from the group consisting of propylene glycol, butylene glycol, pentylene glycol, hexylene glycol, oligomers of ethylene glycol, oligomers of propylene glycol and mixtures thereof.

* * * * *